United States Patent
Chen et al.

(10) Patent No.: US 10,317,296 B2
(45) Date of Patent: Jun. 11, 2019

(54) METHOD FOR ESTIMATING STRESS OF ELECTRONIC COMPONENT

(71) Applicant: Winbond Electronics Corp., Taichung (TW)

(72) Inventors: Chien-Chang Chen, Hualien County (TW); Horng-Shing Lu, Hsinchu (TW)

(73) Assignee: Winbond Electronics Corp., Taichung (TW)

( * ) Notice: Subject to any disclaimer, the term of this patent is extended or adjusted under 35 U.S.C. 154(b) by 111 days.

(21) Appl. No.: 14/988,747

(22) Filed: Jan. 6, 2016

(65) Prior Publication Data
US 2016/0379905 A1 Dec. 29, 2016

(30) Foreign Application Priority Data
Jun. 25, 2015 (CN) .......................... 2015 1 0356926

(51) Int. Cl.
*G01B 3/44* (2006.01)
*G01L 1/00* (2006.01)
(Continued)

(52) U.S. Cl.
CPC .............. *G01L 1/005* (2013.01); *H01L 22/12* (2013.01); *G01N 25/16* (2013.01)

(58) Field of Classification Search
CPC ......... H01L 22/30; G01L 1/005; G01L 25/00; G01L 27/00; G01N 25/00; G01N 27/00
See application file for complete search history.

(56) References Cited

U.S. PATENT DOCUMENTS 6,245,583 B1 * 6/2001 Amador ............... H01L 21/563
257/E21.503
7,471,381 B2 12/2008 Xu et al.
(Continued)

FOREIGN PATENT DOCUMENTS

CN 101060088 10/2007
CN 101118851 2/2008
(Continued)

OTHER PUBLICATIONS

"Office Action of Taiwan Counterpart Application", dated Jul. 19, 2016, p. 1-p. 3, in which the listed reference were cited.
(Continued)

*Primary Examiner* — Toan K Lee
(74) *Attorney, Agent, or Firm* — JCIPRNET

(57) ABSTRACT

A method for estimating stress of an electronic component. An electronic component including first and second elements and conductive bumps is provided. Each conductive bump has two surfaces connected to the first and second elements respectively. Two adjacent conductive bumps have a pitch therebetween. The conductive bumps includes a first conductive bump and second conductive bumps. A stress value of the first conductive bump related to a testing parameter is calculated. A stress value of each second conductive bump related to the testing parameter is calculated according to a first calculating formula. The first calculating formula is $$\sigma_2 = \frac{L}{D-2r}\sigma_1,$$

$\sigma_2$ is the stress of each second conductive bump, L is a beeline distance between each second conductive bump and
(Continued)

the first conductive bump, D is an average value of the pitches of the conductive bumps, r is a radius of each surface, and $\sigma_1$ is the stress value of the first conductive bump.

5 Claims, 4 Drawing Sheets

(51) Int. Cl.
    *H01L 21/66*     (2006.01)
    *G01N 25/16*     (2006.01)

(56) References Cited

U.S. PATENT DOCUMENTS

| | | | |
|---|---|---|---|
| 2002/0024110 A1* | 2/2002 | Iwatsu | H01L 21/563 257/459 |
| 2004/0188862 A1* | 9/2004 | Nagarajan | H01L 21/563 257/787 |
| 2005/0006759 A1* | 1/2005 | Huang | H01L 24/11 257/734 |
| 2007/0023920 A1* | 2/2007 | Jao | H01L 23/367 257/778 |
| 2008/0099890 A1* | 5/2008 | Chen | H01L 23/3128 257/666 |
| 2010/0073022 A1 | 3/2010 | Schnetker | |
| 2011/0147927 A1* | 6/2011 | Hagihara | H01L 24/03 257/737 |
| 2013/0067424 A1 | 3/2013 | Yamamoto et al. | |
| 2013/0249105 A1* | 9/2013 | Lin | H01L 23/3157 257/774 |
| 2013/0295697 A1 | 11/2013 | Hanan et al. | |
| 2016/0086902 A1* | 3/2016 | Lu | H01L 24/14 257/737 |

FOREIGN PATENT DOCUMENTS

| | | |
|---|---|---|
| CN | 101739490 | 6/2010 |
| CN | 102281715 | 12/2011 |
| CN | 102782866 | 11/2012 |
| CN | 103778292 | 5/2014 |
| CN | 103810364 | 5/2014 |
| TW | 200409258 | 6/2004 |
| TW | 201036174 | 10/2010 |
| TW | 201505168 | 2/2015 |
| TW | 201506113 | 2/2015 |

OTHER PUBLICATIONS

Tian Yanhong et al., "Influence of the Hybrid BGA Residuals Stress after Reflow on the Thermal Cycling Reliability", Journal of Mechanical Engineering, Jan. 2014, pp. 86-91.

Gao Qi et al., "Study of the Thermal Field and Thermal Stress Field of Typical BGA Packaging by Numerical Simulation", International Conference on Electronic Packaging Technology, Dec. 2014, pp. 971-975.

"Office Action of China Counterpart Application", dated Apr. 2, 2018, p. 1-p. 5.

* cited by examiner

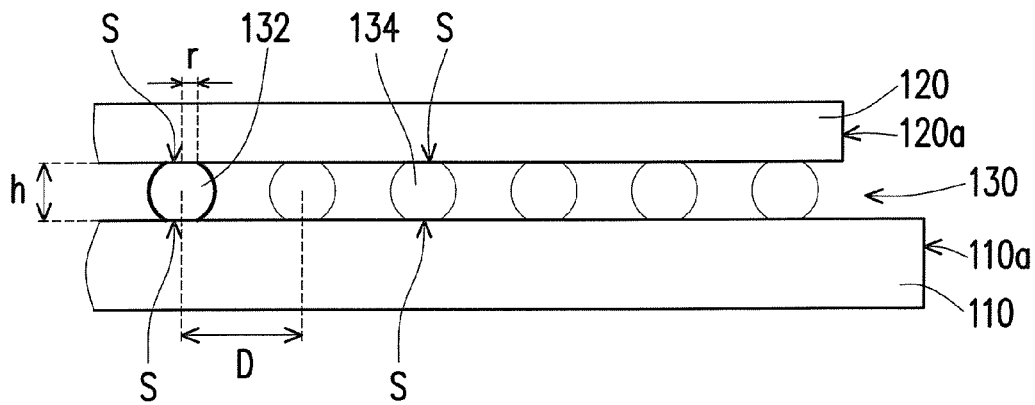

Providing an electronic component including a first element, a second element and a plurality of conductive bumps, wherein each of the conductive bumps has two opposite surfaces, the two surfaces are respectively connected to the first element and the second element, a pitch is between adjacent two of the conductive bumps, and the conductive bumps includes a first conductive bump and a plurality of second conductive bumps — S602

Calculating a stress value of the first conductive bump related to a testing parameter — S604

Calculating a stress value of each of the second conductive bumps related to a testing parameter according to a first calculating formula, wherein the first calculating formula is , $\sigma_2 = \frac{L}{D-2r} \sigma_1$, $\sigma_2$ is the stress value of each of the second conductive bumps, L is a distance between each of the second conductive bumps and the first conductive bump, D is an average of the pitches of the conductive bumps, r is a radius of each of the surfaces, and $\sigma_1$ is the stress value of the first conductive bump — S606

FIG. 3

METHOD FOR ESTIMATING STRESS OF ELECTRONIC COMPONENT

CROSS-REFERENCE TO RELATED APPLICATION

This application claims the priority benefit of Chinese application serial no. 201510356926.9, filed on Jun. 25, 2015. The entirety of the above-mentioned patent application is hereby incorporated by reference herein and made a part of this specification.

BACKGROUND

Field of the Invention

The invention is directed to a method for estimating stress of an electronic component and more particularly, to a method for estimating propagating stress of an electronic component.

Description of Related Art

In a semiconductor packaging process, a chip is commonly disposed on a substrate, and conductive bumps (e.g., solder balls) are often used as a bonding medium for the chip and the substrate. Although the bonding method using the conductive bumps has low cost and is easy for manufacturing, coefficients of thermal expansion (CTEs) of bonding surfaces are different. Fatigue effect resulted from repetitive changes in temperature or voltage during system operation is mainly the reason for damage to bonding points of the chip. Fatigue failure may be classified into mechanical fatigue failure and thermal fatigue failure. Mechanical fatigue failure is due to continuous transformation and movement, resulting in a decrease in mechanical strength. Thermal fatigue failure, on the other hand, is caused by poor match of coefficients of thermal expansion between two surfaces, resulting in the two surfaces pulling each other because of minor transformation generated at high and low temperatures, which, under long term influences, may easily cause the surfaces to peel off. As such, both the chip and the substrate under the chip would be damaged, which leads to the reduction in effectiveness and reliability of the chip package structure.

Accordingly, a stress generated to each conductive bump under a certain temperature or voltage variation condition in the semiconductor package is commonly calculated by utilizing finite element simulation at present, so as to estimate a lifetime of each conductive bump. However, the finite element simulation has a complicated calculation process and consumes much computing time. Therefore, how to rapidly estimate the stress and lifetime of each conductive bump in the semiconductor package has become an important subject in the art.

SUMMARY

The invention provides a method for estimating stress of an electronic component, which can facilitate in rapidly estimating the propagating stress of conductive bumps of the electronic component.

A method for estimating stress of an electronic component provided by the invention include the following steps. An electronic component including a first element, a second element and a plurality of conductive bumps is provided. Each of the conductive bumps has two opposite surfaces, and the two surfaces are respectively connected to the first element and the second element, adjacent two of the conductive bumps have a pitch therebetween, and the conductive bumps include a first conductive bump and a plurality of second conductive bumps. A stress value of the first conductive bump related to a testing parameter is calculated. A stress value of each of the second conductive bumps related to the testing parameter is calculated according to a first calculating formula. The first calculating formula is $$\sigma_2 = \frac{L}{D-2r}\sigma_1,$$

$\sigma_2$ is the stress value of each of the second conductive bumps, L is a beeline distance between each of the second conductive bumps and the first conductive bump, D is an average of the pitches of the conductive bumps, r is a radius of each of the surfaces, and $\sigma_1$ is the stress value of the first conductive bump.

To sum up, in the method for estimating stress of the invention, an estimating concept according to the first calculating formula, $$\sigma_2 = \frac{L}{D-2r}\sigma_1,$$

lies in that the stresses received by the conductive bumps gradually propagate toward and are accumulated at the surrounding second conductive bumps from the first conductive bump as the center. Therefore, the second conductive bump with the greater distance from the first conductive bump has the greater accumulated propagating stress. Based on this concept, in the invention, the stress value $\sigma_1$ of a single conductive bump (i.e., the first conductive bump) in the electronic component is first calculated according to the set testing parameter, and the stress value $\sigma_1$ is then substituted to the first calculating formula, so as to calculate the stress value $\sigma_2$ of each of the other conductive bumps (i.e., the second conductive bumps) related to the testing parameter. Thereby, the stress values of all the conductive bumps can be calculated rapidly to effectively estimate the lifetime of the electronic component, without utilizing finite element simulation, which has a complicated calculation process and consumes much computing time.

In order to make the aforementioned and other features and advantages of the invention more comprehensible, several embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

FIG. 2 is a cross-sectional view of the electronic component depicted in FIG. 1 along a line I-I.

FIG. 3 is a flowchart illustrating a method for estimating stress of an electronic component according to an embodiment of the invention.

DESCRIPTION OF EMBODIMENTS

Figure 1:
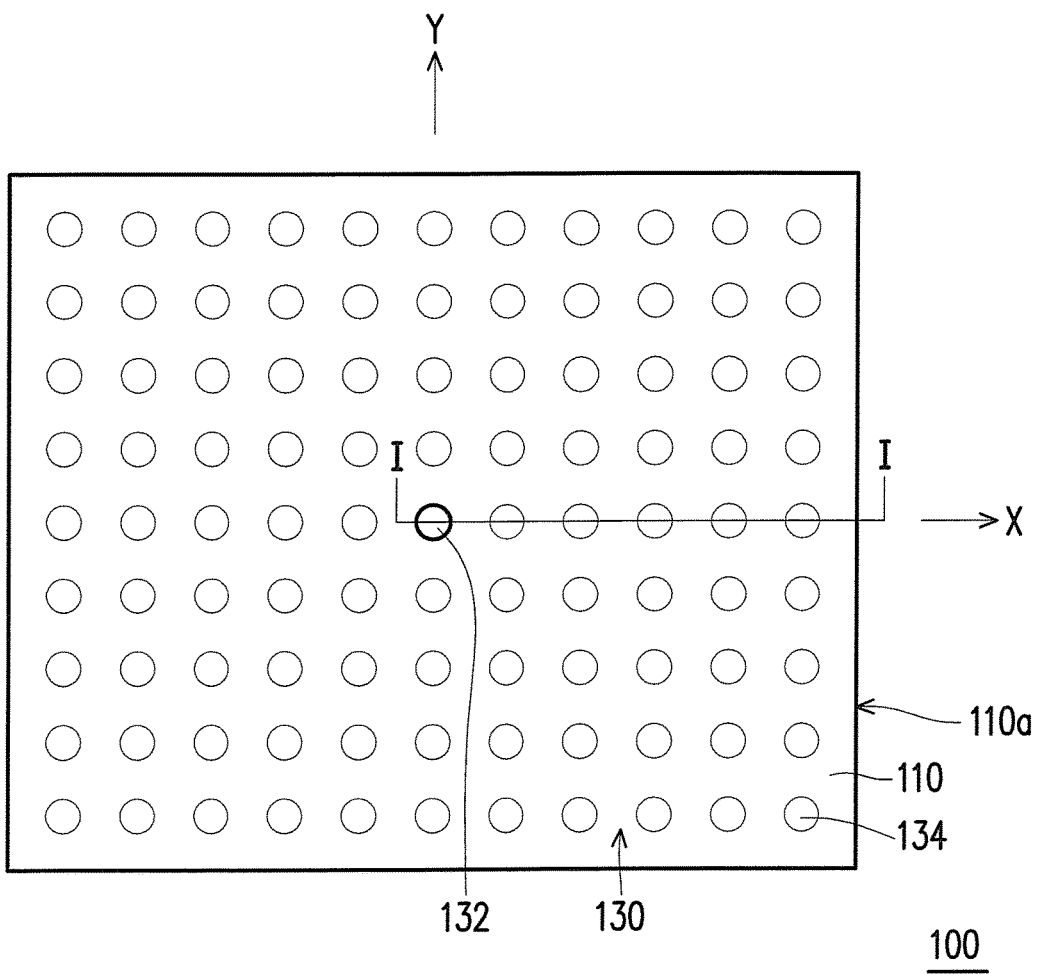
FIG. 1 is a top view illustrating an electronic component according to an embodiment of the invention.

Referring to FIG. 1 through FIG. 3, a method for estimating stress of an electronic component of the present embodiment includes the following steps. First, an electronic component 100 as illustrated in FIG. 1 and FIG. 2 is provided. The electronic component 100 includes a first element 110, a second element 120 and a plurality of conductive bumps 130. Each of the conductive bumps 130 has two opposite surfaces S, and the two surfaces S are connected to and contact the first element 110 and the second element 120, respectively. A radius of each surface is r. Each of the conductive bumps 130 and another conductive bump 130 adjacent thereto have a pitch therebetween, and an average of the pitches of the conductive bumps 130 is D (step S602).

In the present embodiment, the electronic component 100 has, for example, a semiconductor structure, and the first element 110 and the second element 120 are, for example, a substrate and a chip in the semiconductor structure respectively, but the invention is not limited thereto. Additionally, in the present embodiment, the conductive bumps 130 are arranged equidistantly, for example, such that the pitch values of all the conductive bumps 130 are D, but the invention is not limited thereto. In other embodiments, the conductive bumps 130 may be irregularly arranged, have pitches with various sizes, and an average of the pitches is D.

In order to describe the method for estimating stress of the present embodiment conveniently, the conductive bumps 130 is divided into a central first conductive bump 132 and a plurality of second conductive bumps 134 surrounding the first conductive bump 132. Namely, the conductive bumps 130 include a first conductive bump 132 and a plurality of second conductive bumps 134. The first conductive bump 132 is located in, a geometric center of the electronic component 100, and the second conductive bumps 134 are distributed between the first conductive bump 132 and a peripheral edge of the electronic component 100. The peripheral edge is, for example, a peripheral edge 110a of the first element 110 or a peripheral edge 120a of the second element 120.

Then, a stress value of the first conductive bump 132 related to a testing parameter $\sigma_1$ is calculated (step S604). The testing parameter is a parameter set for applying a temperature cycle variation, a voltage cycling test or other types of testing conditions to the electronic component 100, for example, which is not limited in the invention. Namely, the testing parameter may be a temperature variation, a voltage variation or a variation of other testing values. Thereafter, a stress value $\sigma_2$ of each second conductive bump 134 related to the testing parameter is calculated based on the calculated stress value $\sigma_1$ of the first conductive bump 132 according to a first calculating formula. The first calculating formula is $$\sigma_2 = \frac{L}{D-2r}\sigma_1,$$

where $\sigma_2$ is the stress value of each second conductive bump 134, L is a beeline distance between each second conductive bump 134 and the first conductive bump 132, D is the average of the pitches of the conductive bumps 130, r is the radius of each surface, and $\sigma_1$ if the stress value of the first conductive bump 132 (step S606).

An estimating concept according to the first calculating formula lies in that the stresses received by the conductive bumps 130 may gradually propagate toward and be accumulated at the surrounding second conductive bumps 134 from the first conductive bump 132 as the center. Thus, the second conductive bump 134 with the greater distance from the first conductive bump 132 has the greater accumulated propagating stress. Based on this concept, in the present embodiment, the stress value $\sigma_1$ of a single conductive bump 130 (i.e., the first conductive bump 132) in the electronic component 100 is first calculated according to the set testing parameter, and the stress value $\sigma_1$ is then substituted to the first calculating formula, so as to calculate the stress value $\sigma_2$ of each of the other conductive bumps 130 (i.e., the second conductive bumps 134) related to the testing parameter. Thereby, the stress values of all the conductive bumps 130 can be calculated rapidly to effectively estimate the lifetime of the electronic component 100, without utilizing finite element simulation, which has a complicated calculation process and consumes much computing time.

In step S604 illustrated in FIG. 3, the stress value $\sigma_1$ of the first conductive bump 132 related to the testing parameter is calculated according to a second calculating formula. The second calculating formula is $$\sigma_1 = \frac{E_{solder}(D-2r)\Delta\alpha\Delta T}{4(1+\in_{solder})h},$$

where $E_{solder}$ is a Young's modulus of each conductive bump 130, $\in_{solder}$ is a Poisson ratio of each conductive bump 130, $\Delta\alpha$ is a difference between a coefficient of thermal expansion (CTE) of the first element 110 and a CTE of the second element 120, h is a distance between the first element and the second element. In addition, $\Delta T$ is a testing parameter set for applying a temperature cycle variation, a voltage cycling test or other types of testing conditions to the electronic component 100. An embodiment is provided below as an example and will be described with reference to FIG. 4 hereinafter.

Figure 4:
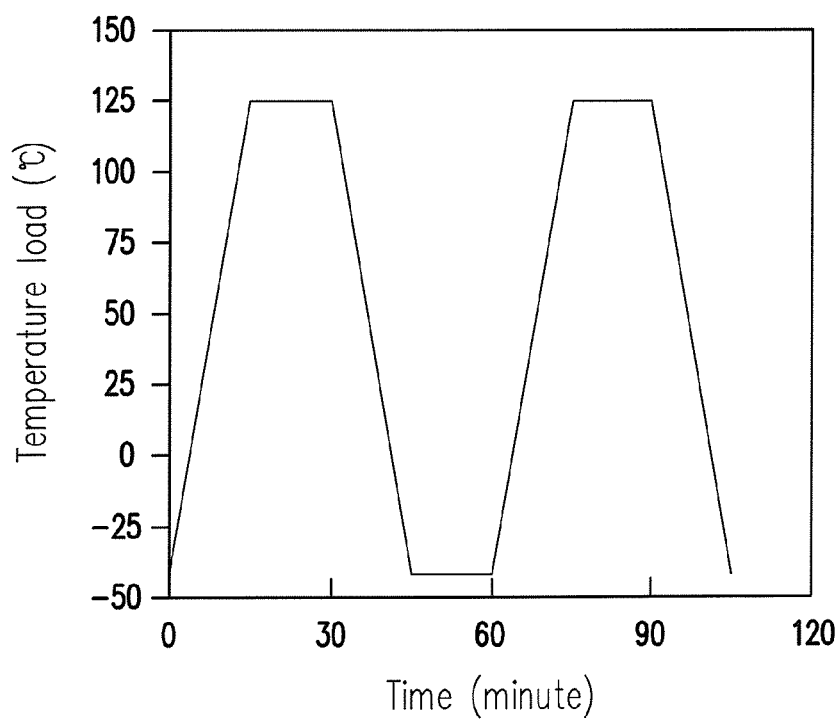
FIG. 4 illustrating testing conditions of FIG. 3.

Referring to FIG. 4, the testing condition of the present embodiment is to apply a temperature cycle variation to the electronic component 100, and $\Delta T$ is a parameter set according to the temperature cycle variation. A period of the temperature cycle variation is, for example, 60 minutes, and a maximum and a minimum temperatures are respectively 125 and 140° C., for example. In other embodiments, the temperature cycle variation may be set to have other suitable periods, other suitable temperature variations and temperature values, which is not limited in the invention. In addition, the testing condition may also be changed to apply a voltage cycling test or other types of testing conditions to the electronic component 100, so as to set the testing parameter, which is not limited in the invention.

The estimating concept according to the first calculating formula in step S606 depicted in FIG. 3 will be described in detail hereinafter. For descriptive convenience, a coordinated position of the first conductive bump 132 at the intersection of the X and the Y axes in FIG. 1 and the stress value $\sigma_1$ are respectively defined as (0, 0) and $\sigma_{(0,0)}$, while a coordinate position of each second conductive bump 134 and the stress value $\sigma_2$ in the two dimensional (2D) coordinate system formed by the X and the Y axes are respectively defined as (i, j) and $\sigma_{(i,j)}$, where the stress value $\sigma_2$ of each second conductive bump 134 on the X axis is $\sigma_{(i,0)}$, and the stress value $\sigma_2$ of each second conductive bump 134 on the Y axis is $\sigma_{(0,j)}$. A greater absolute value of i or j represents a greater distance between the corresponding second conductive bump 134 and the first conductive bump 132. Accordingly, the stresses received by the conductive bumps 130 gradually propagate toward and are accumulated at the surrounding second conductive bumps 134 from the first conductive bump 132 as the center, such that the second conductive bump 134 with the greater distance from the first conductive bump 132 has the greater accumulated propagating stress. Thus, based on this propagating concept, $\sigma_{(i,0)}$ is approximated to $N_1\sigma_{(0,0)}$, $\sigma_{(0,j)}$ is approximated to $N_2\sigma_{(0,0)}$, a geometry relation of $\sigma_{(i,j)}$ is $\sqrt{\sigma_{(i,0)}^2 + \sigma_{(0,j)}^3}$, where $N_1$ and $N_2$ are respectively equal to $$\frac{\Delta x}{D-2r} \text{ and } \frac{\Delta y}{D-2r},$$

$\Delta x$ is a distance from the corresponding second conductive bump 134 to the first conductive bump 132 on the X axis, and $\Delta y$ is a distance from the corresponding second conductive bump 134 to the first conductive bump 132 on the Y axis. A calculating formula, $$\sigma_{(i,j)} = \frac{\sqrt{\Delta x^2 + \Delta y^2}}{D-2r}\sigma_{(0,0)},$$

equivalent to the first calculating formula, $$\sigma_2 = \frac{L}{D-2r}\sigma_1,$$

used in step S606 illustrated in FIG. 3 may be obtained by deriving according to the aforementioned approximation manner.

In the present embodiment, a lifetime of each second conductive bump 134 may be further estimated according to the stress value $\sigma_2$ of each second conductive bump 134, of which is specific method is described as follows. A creep rate of each second conductive bump is calculated based on the stress value $\sigma_2$ of each second conductive bump 134 according to a third calculating formula. The third calculating formula is $\varepsilon \cong \int \dot{\varepsilon}_{total} + \delta\dot{\varepsilon}_{transn} dt$, where $\varepsilon$ is the creep rate of each second conductive bump, $$\dot{\varepsilon}_{total} = \frac{D_{L0}}{d^2}\left(e^{-\frac{Q_{NH}}{kT(t)}} + \frac{D_{G0}\delta}{D_{L0}d}e^{-\frac{Q_C}{kT(t)}}\right)\exp\left(-\frac{Q_f}{kT(t)}\right)\sinh\left(\frac{\sigma_2\Omega}{kT(t)}\right),$$

$$\delta\dot{\varepsilon}_{trasn} = \frac{1}{\eta}\{\dot{\varepsilon}(t' + \eta P) - \dot{\varepsilon}(t')\},$$

$D_{L0}$ is a lattice diffusion coefficient, d is a grain size, $Q_{NH}$ is a Nabarro-Herring type vacancy migration energy, $D_{G0}$ is a grain boundary diffusion coefficient, $\delta$ is an effective width of a grain boundary, $Q_C$ is a Coble type vacancy migration energy, $Q_f$ is a vacancy formation energy, k is a Boltzmann's constant, $\Omega$ is an atomic volume, P is a number of testing cycles, $\eta$ is a parameter of testing cycle percentage, and T(t) and $\dot{\varepsilon}(t')$ are testing functions. T(t) and $\dot{\varepsilon}(t')$ are, for example, functions corresponding to the testing condition illustrated in FIG. 4, where a single period of the temperature cycle function illustrated in FIG. 4 is 60 minutes which is divided into four temperature condition zones of 15 minutes. Namely, a time length of one temperature condition zone is 0.25 times a time length of the single period, and accordingly, the parameter of testing cycle percentage, $\eta$, is defined as 0.25.

Figure 5:
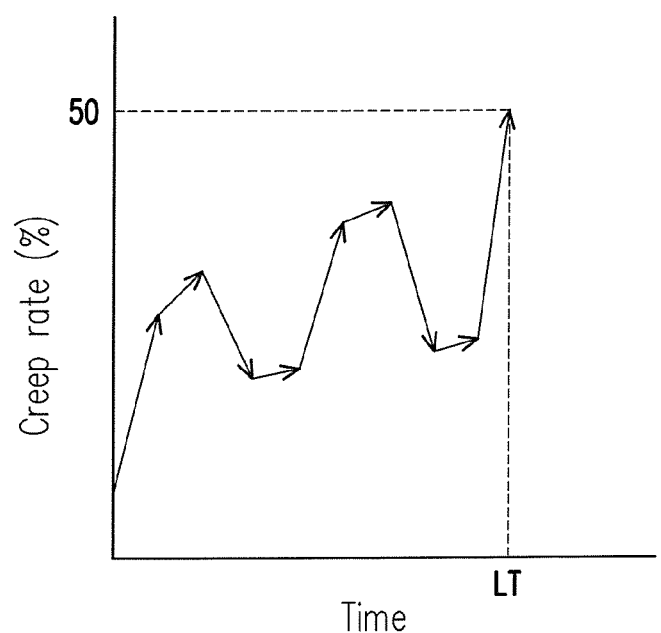
FIG. 5 illustrates the creep rate of each second conductive bump depicted in FIG. 1 varies with time.

FIG. 5 illustrates the creep rate of each second conductive bump depicted in FIG. 1 varies with time. According to the third calculating formula, a creep rate $\varepsilon$ of each second conductive bump 134 at each time point may be calculated, as illustrated in FIG. 5, for example, and the lifetime of each second conductive bump 134 may be accordingly estimated. For example, the creep rate $\varepsilon$ of each second conductive bump 134 will be considered as invalid if rising up to 50%, and thus, the lifetime of each second conductive bump 134 may be estimated as corresponding LT.

A table of comparing the lifetime of each conductive bump which is estimated according to the aforementioned manner with actually experiment results is provided below. Therein, the estimation and the experiment are performed, for example, under a testing condition that $E_{solder}$ is 22 Gpa, $\varepsilon_{solder}$ is 0.35, D is 1 mm, h is 0.12 mm, $\Delta\alpha$ is 17.6 ppm/° C. with reference to the testing conditions illustrated in FIG. 4, and the estimated and experimented results of the second conductive bumps 134 having coordinates of (2, 2), (4, 3), (6, 5) as illustrated in FIG. 1 are compared.

| Coordinate | Estimated lifetime (HR) | Experimented lifetime (HR) |
|---|---|---|
| (2, 2) | 438 | 450 |
| (4, 3) | 206 | 200 |
| (6, 5) | 93 | 95 |

According to the comparison table, the lifetime of each conductive bump which is estimated according to the aforementioned manner has not much difference from the actual experimented results and is in line with expectations.

Figure 6:
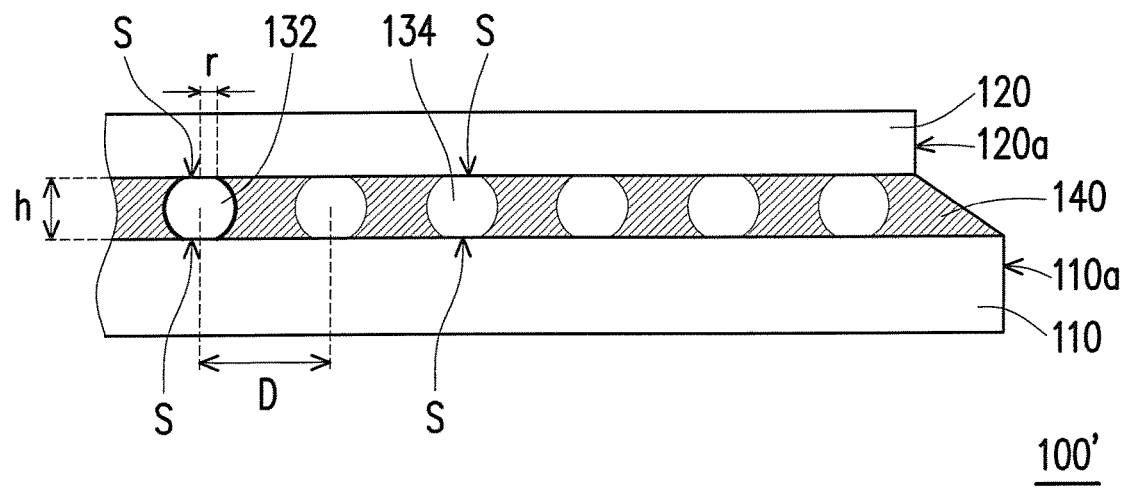
FIG. 6 is a partially cross-sectional view illustrating an electronic component according to another embodiment of the invention.

FIG. 6 is a partially cross-sectional view illustrating an electronic component according to another embodiment of the invention. An electronic component 100' illustrated in FIG. 6 is different from the electronic component 100 illustrated in FIG. 2 in the electronic component 100' further including a molding compound 140. The molding compound 140 is disposed between the first element 110 and the second element 120 and covers the conductive bumps 130. Based on the disposition difference, the stress value $\sigma_2$ of each second conductive bump 134 related to the testing parameter is calculated according to a fourth calculating formula in replacement with the first calculating formula. The fourth calculating formula is $$\sigma_2 = \frac{L}{D-2r}(\sigma_1 - (E_{solder}\alpha_{solder} + E_{underfill}\alpha_{underfill})\Delta T),$$

$E_{underfill}$ is a Young's modulus of the molding compound, $\alpha_{underfill}$ is a CTE of the molding compound, and D, r, L, $E_{solder}$, $\alpha_{solder}$ and $\Delta T$ are defined as above.

To summarize, in the method for estimating stress of the invention, the estimating concept according to the first calculating formula, $$\sigma_2 = \frac{L}{D-2r}\sigma_1,$$

lies in that the stresses received by the conductive bumps gradually propagate toward and are accumulated at the surrounding second conductive bumps from the first conductive bump as the center. Therefore, the second conductive bump with the greater distance from the first conductive bump has the greater accumulated propagating stress. Based on this concept, in the invention, the stress value of a single conductive bump (i.e., the first conductive bump) in the electronic component is first calculated according to the set testing parameter, and the stress value $\sigma_1$ is then substituted to the first calculating formula, so as to calculate the stress value $\sigma_2$ of each of the other conductive bumps (i.e., the second conductive bumps) related to the testing parameter. Thereby, the stress values of all the conductive bumps can be calculated rapidly to effectively estimate the lifetime of the electronic component, without utilizing finite element simulation, which has a complicated calculation process and consumes much computing time.

Although the invention has been described with reference to the above embodiments, it will be apparent to one of the ordinary skill in the art that modifications to the described embodiment may be made without departing from the spirit of the invention. Accordingly, the scope of the invention will be defined by the attached claims not by the above detailed descriptions.

What is claimed is:

1. A testing method for an electronic component within a semiconductor package, the method comprising:
   providing an electronic component comprising a first element, a second element and a plurality of conductive bumps, wherein each of the conductive bumps has two opposite surfaces, the two surfaces are respectively connected to the first element and the second element, a pitch is between adjacent two of the conductive bumps, and the conductive bumps comprises a first conductive bump and a plurality of second conductive bumps;
   applying a testing parameter associated with a testing condition variation to the electronic component to obtain a testing result;
   calculating a stress value of the first conductive bump based on the testing result;
   calculating a stress value of each of the second conductive bumps by a processor, wherein the processor uses a first calculating formula to calculate the stress value of each of the second conductive bumps related to the testing parameter, the first calculating formula is $$\sigma_2 = \frac{L}{D-2r}\sigma_1,$$

$\sigma_2$ is the stress value of each of the second conductive bumps, L is a beeline distance between each of the second conductive bumps and the first conductive bump, D is an average of the pitches of the conductive bumps, r is a radius of each of the surfaces, and $\sigma_1$ is the stress value of the first conductive bump; and
   determining the stress value of each of the second conductive bumps without having to measure the stress value of each of the second conductive bumps, and estimating a lifetime of each of the second conductive bumps according to the stress value of each of the second conductive bumps.

2. The method according to claim 1, wherein the first conductive bump is located in a geometric center of the electronic component.

3. The method according to claim 1, wherein the testing parameter is a temperature variation or a voltage variation.

4. The method according to claim 1, wherein the step of calculating the stress value of the first conductive bump related to the testing parameter comprises:
   calculating the stress value of the first conductive bump related to the testing parameter according to a second calculating formula, wherein the second calculating formula is $$\sigma_1 = \frac{E_{solder}(D-2r)\Delta\alpha\Delta T}{4(1+\in_{solder})h},$$

$E_{solder}$ is a Young's modulus of each of the conductive bumps, $\in_{solder}$ is a Poisson ratio of each of the conductive bumps, $\Delta\alpha$ is a difference between a coefficient of thermal expansion (CTE) of the first element and a CTE of the second element, h is a distance between the first element and the second element, and $\Delta T$ is the testing parameter.

5. A testing method for testing an electronic component within a semiconductor package, the method comprising:
   providing an electronic component comprising a first element, a second element, a plurality of conductive bumps, and a molding compound, wherein the molding compound is disposed between the first element and the second element and covers the conductive bumps, each of the conductive bumps has two opposite surfaces, the two surfaces are respectively connected to the first element and the second element, a pitch is between adjacent two of the conductive bumps, and the conductive bumps comprises a first conductive bump and a plurality of second conductive bumps;
   applying a testing parameter associated with a testing condition variation to the electronic component to obtain a testing result;
   calculating a stress value of the first conductive bump based on the testing result;
   calculating a stress value of each of the second conductive bumps by a processor, wherein the processor uses a fourth calculating formula to calculate the stress value of each of the second conductive bumps related to the testing parameter, the fourth calculating formula is $$\sigma_2 = \frac{L}{D-2r}(\sigma_1 - (E_{solder}\alpha_{solder} + E_{underfill}\alpha_{underfill})\Delta T),$$

$E_{solder}$ is a Young's modulus of each of the conductive bumps, $\alpha_{solder}$ is a coefficient of thermal expansion (CTE) of each of the conductive bumps, $E_{underfill}$ is a Young's modulus of the molding compound, $\alpha_{underfill}$ is a CTE of the molding compound, and $\Delta T$ is the testing parameter; and
   estimating a lifetime of each of the second conductive bumps according to the stress value of each of the second conductive bumps.

* * * * *